United States Patent [19]

Huang et al.

[11] Patent Number: 4,659,711

[45] Date of Patent: Apr. 21, 1987

[54] 1,2,3,4-TETRAHYDROPHTHALAZINE AND HEXAHYDROPYRIDAZINE COMPOUNDS FOR TREATING HYPERTENSION

[75] Inventors: Fu-chin Huang, Boonton, N.J.; Howard Jones, Ossining; Wan-Kit Chan, Yorktown Heights, both of N.Y.

[73] Assignee: USV Pharmaceutical Corporation, Tuckahoe, N.Y.

[21] Appl. No.: 785,086

[22] Filed: Oct. 4, 1985

Related U.S. Application Data

[63] Continuation of Ser. No. 462,644, Jan. 31, 1983, abandoned.

[51] Int. Cl.$^4$ .................... C07D 237/04; A61K 31/50
[52] U.S. Cl. .................... 514/247; 514/248; 544/224; 544/238; 544/239; 544/237; 548/378
[58] Field of Search ............... 544/238, 224, 239, 224, 544/237; 514/248, 247

[56]  References Cited

U.S. PATENT DOCUMENTS

| | | | |
|---|---|---|---|
| 4,288,368 | 9/1981 | Haugwitz | 260/326.35 |
| 4,303,583 | 12/1981 | Kim et al. | 260/239.3 T |
| 4,331,806 | 5/1982 | Haugwitz | 424/250 |
| 4,344,949 | 8/1982 | Hoefle et al. | 424/258 |
| 4,374,829 | 2/1983 | Harris et al. | 260/112.5 R |
| 4,465,679 | 8/1984 | Huang et al. | 514/218 X |

OTHER PUBLICATIONS

Hackh's Chemical Dictionary, p. 363.

*Primary Examiner*—Donald G. Daus
*Assistant Examiner*—William A. Teoli, Jr.

[57]  ABSTRACT

Compounds of the general formula

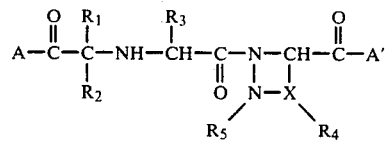

and their pharmaceutically-acceptable salts, wherein the substituents are as defined herein, having antihypertensive activity.

18 Claims, No Drawings ary-butyl, amyl, iso-amyl, hexyl, octyl, and the like.
1,2,3,4-TETRAHYDROPHTHALAZINE AND HEXAHYDROPYRIDAZINE COMPOUNDS FOR TREATING HYPERTENSION This application is a continuation of our previous copending application Ser. No. 462,644 filed Jan. 31, 1983, now abandoned.

BACKGROUND OF THE INVENTION

This application relates to compounds, their pharmaceutically acceptable salts, and pharmaceutical preparations made therefrom, having biological activity as inhibitors of the enzymatic conversion of angiotensin I to angiotensin II. The products comprising the present invention have utility in the treatment of hypertension in subjects suffering therefrom.

SUMMARY OF THE INVENTION

Broadly stated, the present invention comprises compounds of the formula

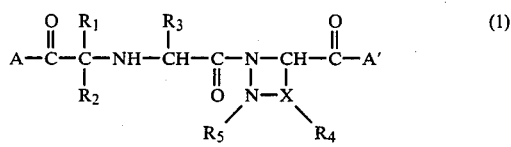

and their pharmaceutically-acceptable salts, wherein
X is a saturated or unsaturated chain of 1 to 5 carbon atoms;
A and A' are independently hydroxy, alkoxy, aryloxy, or hydroxyamino;
$R_1$, $R_2$, $R_3$, and $R_4$ are independently hydrogen, alkyl, aryl, aralkyl, fused cycloalkyl-aryl, fused arylcycloalkyl, aryloxyalkyl, arylalkyloxyalkyl, polycyclic aryl, alkenyl, alkynyl, fused cycloalkylarylalkyl, fused aryl-cycloalkyl-alkyl, polycyclic aryl, cycloalkyl, or cycloalkyl-alkyl; and $R_4$ can in addition be keto-oxygen or, when X contains at least 2 carbon atoms, $R_4$ can be an aryl ring or a cycloalkyl ring fused to X;
$R_5$ can be a second bond to the adjacent carbon atom, hydrogen, alkyl, alkenyl, alkynyl, acyl, cycloalkyl, cycloalkyl-alkyl, polycycloalkyl, polycycloalkylalkyl, aryl, aralkyl, polycyclic aryl, fused cycloalkyl-aryl, fused arylcycloalkyl, fused arylcycloalkyl-alkyl, or fused cycloalkylaryl-alkyl;
wherein the alkyl, alkoxy, alkenoxy, alkenyl, and alkynyl groups may carry substituents selected from the group consisting of hydroxy, acyloxy, aryl, alkoxy, aryloxy, amino, mono- or dialkylamino, acylamino, mercapto, alkylthio, and mercaptoalkyl; the cycloalkyl rings may include one or more hetero atoms, may be saturated or unsaturated, and may carry substituents selected from the group consisting of alkyl, hydroxy, alkylamino, and nitro; and the aryl rings may contain one or more hetero atoms and may carry substituents selected from the group consisting of carboxylic acid, cyano, carboxy-lower alkoxy, alkyl, hydroxy, alkoxy, hydroxyalkyl, halo, trifluoroalkyl, thio, alkylmercapto, thioalkyl, amino, alkylamino, aminoalkyl, nitro, methylenedioxy, and sulfamyl;
wherein the alkyl groups contain 1 to 9 carbon atoms; and the cycloalkyl groups and the cycloalkyl portions of substituents containing cycloalkyl groups contain 3 to 9 carbon atoms.

DESCRIPTION OF THE PREFERRED EMBODIMENTS

Preferred compounds of the present invention are those of the general formula given above in which A and A' are each hydroxy or lower alkoxy; $R_1$, $R_2$, $R_3$, $R_4$, and $R_5$ are each hydrogen, alkyl, aryl, aralkyl, cycloalkyl, or w-aminoalkyl wherein the amino is mono- or disubstituted with hydrogen, alkyl, aryl, or aralkyl, or is incorporated in a saturated or unsaturated one- or two-ring heterocyclic moiety containing preferably up to 12 atoms in the ring. Included as preferred groups are groups in which $R_5$ provides diuretic activity to the compound (1), e.g. sulfonamido-chloro-phenyl. Included as preferred $R_4$ groups are those which are fused with X to form an aryl or cycloalkyl ring, having the general structure

The alkyl groups per se and the alkyl moieties in alkoxy, aralkyl, cycloalkyl, aminoalkyl, and the like, may be straight-chained or branched and preferably contain from 1 to 9 carbon atoms. Such groups include methyl, ethyl, propyl, isopropyl, butyl, isobutyl, tertiPreferably the alkyl groups are lower alkyl, which term shall refer to alkyl groups containing from 1 to 6 carbon atoms, straight-chained or branched.

The alkenyl and alkynyl groups and moieties can also be straight or branched-chained groups containing from 2 to 9, and preferably 2 to 6, carbon atoms. Such groups include vinyl, ethynyl, propenyl, isopropenyl, and the like.

The acyl groups include such groups as alkanoyl, aroyl, and aralkanoyl, wherein the alkyl and aryl moieties are as defined herein, as well as sulfonyl, sulfamoyl, carbamoyl, and the like, optionally containing an alkyl moiety with 1 to 9 and preferably 1 to 6 carbon atoms.

The preferred subsitutents on the above alkyl, alkenyl, alkynyl, and acyl groups include hydroxy, alkoxy, amino, alkylamino, dialkylamino, mercapto, alkylmercapto, and the like.

The cycloalkyl groups and moieties are saturated or unsaturated and preferably contain 3 to 9 carbon atoms. By "polycycloalkyl" is meant 2 or more fused cycloalkyl rings, having a total of up to 20 carbon atoms. The cycloalkyl, aryl, polycyclic aryl, polycycloalkyl, and fused aryl-cycloalkyl structures can also contain one or more, preferably one or two, hetero atoms, i.e., a sulfur, oxygen, or nitrogen atom, thereby forming a heteroring.

Preferred cyclic and polycyclic ring structures, whether connected directly to the main molecule, connected by an intervening chain, or incorporated with X as

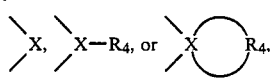

include such radicals as cyclopropyl, cyclobutyl, cyclopentyl, cyclohexyl, cycloheptyl, adamantyl, norbornyl, phenyl, tolyl, benzyl, phenethyl, indolyl, dimethoxyphenyl, hydroxybenzyl, indanyl, naphthyl, tetrahydronaphthyl, decanhydronaphthyl, pyridyl, quinolyl, guanidino, pyrrolidyl, pyrrolyl, morpholinyl, furyl, furfuryl, tetrahydrofurfuryl, benzimidazolyl, thienyl, imidazolyl, and the like. Preferred substituents on the ring structures, i.e., aryl, cycloalkyl, polycyclic aryl, fused arylcycloalkyl, and polycycloalkyl ring structures whether or not containing a hetero atom, include hydroxy, alkyl, alkoxy, aryl, aryloxy, aralkyl, alkylamino, dialkylamino, alkenyl, alkynyl, carboxy, carboalkoxy, cyano, mercapto, amino, alkylthio, mercaptoalkyl, halo, trifluoromethyl, sulfamyl, and the like.

The halo groups include fluoro, chloro, bromo and iodo. Preferred hetero atoms are S, O, and N.

Substituents which are "unsaturated" contain one or more double or triple bond.

Compounds in accordance with the present invention are readily prepared employing known starting materials and procedures. It will be understood by those skilled in the art that the carbons to which $R_1$ and $R_3$ are attached can be asymmetric centers, such that the inventive compounds may exist in SS, SR, RS, and RR forms. Individual isomers and diastereoisomeric mixtures of said forms are within the scope of the invention. The preferred forms have (S,S) configuration.

The compounds of the formula (1) can be prepared by esterifying a compound of the formula (2):

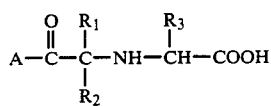
(2)

with e.g. isobutylene in dioxane to form compound (3):

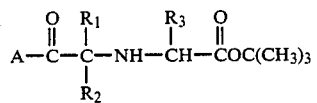
(3)

wherein $R_1$, $R_2$, $R_3$, and A are as defined herein-above. The amino group in compound (3) is then protected, for instance, by reacting compound (3) in pyridine with a suitable protecting group such as 2,2,2-trichloroethyl chloroformate (4):

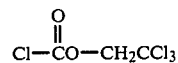
(4)

to form the protected ester compound (5):

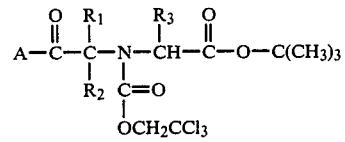
(5)

Compound (5) is then de-esterified, and then converted to e.g. the acid chloride, by reacting compound (5) with strong HCl in dioxane, and then reacting the resultant acid (6):

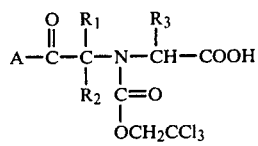
(6)

with, for instance, oxalyl chloride in methylene chloride to form compound (7):

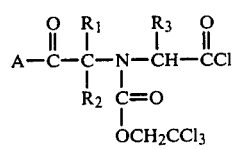
(7)

The cyclic compound with which compound (7) is eventually reacted is formed by reacting compounds of the formula (8):

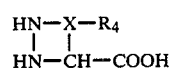
(8)

with e.g. isobutylene and sulfuric acid in dioxane to esterify the —COOH group, and then with a compound of the formula $R_5$—Z where Z is a halogen atom, to form compounds of the formula (9):

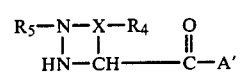
(9)

wherein $R_4$, $R_5$, X and A' are as defined hereinabove. Alternatively, where X comprises a fused ring structure, it is convenient to proceed via the fused ring intermediate, such as compound (10)

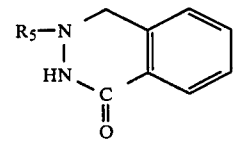
(10)

which is reacted with potassium cyanide in dimethylformamide to form compound (11):

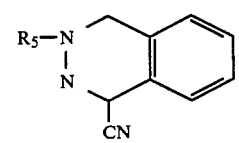
(11)

which is then reacted first with e.g. HCl to convert the —CN group to a —COOH group, then with isobutylene in sulfuric acid to esterify the —COOH group, and finally with hydrogen over Pd/charcoal to form compound (12):

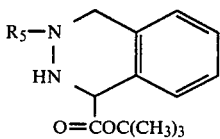

(12)

Compound (7) is reacted in a suitable solvent such as methylene chloride/pyridine with compound (9) or (12) to form compound (13):

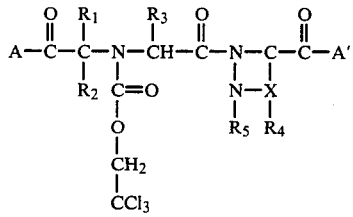

(13)

Compound (13) is de-N-protected with e.g. zinc dust in glacial acetic acid to form compound (1). Where A' forms an ester, the product can be converted to the corresponding acid by bubbling HCl through a solution thereof.

Each of the above reactions proceeds in a straightforward manner in a suitable solvent at temperatures ranging from 0° C. to 150° C.

The products are obtained typically as a mixture of diasteroisomers which can be separated by standard methods of fractional crystallization or chromatography.

The compounds of this invention form acid salts with various inorganic and organic acids which are also within the scope of the invention. The pharmaceutically acceptable acid addition salts of the compounds of the present invention may be prepared by conventional reactions by reacting the free amino acid or amino ester with an appropriate acid providing the desired anion, either in a solvent or medium in which the salt is insoluble, or in water and removing the water by freeze-drying. The salts of strong acids are preferred. As exemplary, but not limiting, of pharmaceutically acceptable acid salts are the salts of hydrochloric, hydrobromic, sulfuric, nitric, acetic, fumaric, malic, maleic and citric acids.

The action of the enzyme renin on angiotensinogen, a pseudoglobulin in blood plasma, produces the decapeptide angiotensin I. Angiotensin I is converted by angiotensin converting enzyme (ACE) to the octapeptide angiotensin II. The latter is an active pressor substance which has been implicated as the causative agent in various forms of hypertension in various mammalian species, e.g., rats and dogs. The compounds of this invention intervene in the renin-to-angiotensin I-to-angiotensin II sequence by inhibiting angiotensin I converting enzyme and reducing or eliminating the formation of the pressor substance angiotensin II and therefore are useful in reducing or relieving hypertension. Thus by the administration of a composition containing one or a combination of compounds of formula (1) or pharmaceutically acceptable salts thereof, hypertension in the species of mammal suffering therefrom is alleviated. A single dose, or preferably two to four divided daily doses, provided on a basis of about 0.1 to 100 mg per kilogram per day, preferably about 1 to 50 mg per kilogram per day, is appropriate to reduce blood pressure.

The substance is preferably administered orally, but a parenteral route such as subcutaneously, intramuscularly, intravenously or intraperitonealy can also be employed.

The compounds of the invention can be utilized to achieve the reduction of blood pressure by formulating one or more of them in compositions such as tablets, capsules or elixirs for oral administration or in sterile solutions or suspensions for parenteral administration. About 10 to 500 mg of a compound or mixture of compounds of formula (1) or physiologically acceptable salt(s) thereof is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Illustrative of the adjuvants which may be incorporated in tablets, capsules and the like are the following: a binder such as gum tragacanth, acacia, corn starch or gelatin; an excipient such as dicalcium phosphate; a disintegrating agent such as corn starch, potato starch, alginic acid and the like; a lubricant such as magnesium stearate; a sweetening agent such as sucrose, lactose or saccharin; a flavoring agent such as peppermint, oil of wintergreen or cherry. When the dosage unit form is a capsule, it may contain in addition to materials of the above type a liquid carrier such as a fatty oil. Various other materials may be present as coatings or to otherwise modify the physical form of the dosage unit. For instance, tablets may be coated with shellac, sugar or both. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a vehicle such as water for injection, a naturally occurring vegetable oil like sesame oil, coconut oil, peanut oil, cottonseed oil, etc., or a synthetic fatty vehicle like ethyl oleate, and the like. Buffers, preservatives, antioxidants and the like can be incorporated as required.

Specific embodiments of the invention are illustrated in the following Examples.

EXAMPLE I

An intermediate employed in the following examples, N-[(1S)-ethoxycarbonyl-3-phenylpropyl]-N-(2,2,2-trichloroethoxycarbonyl)-L-alanine,

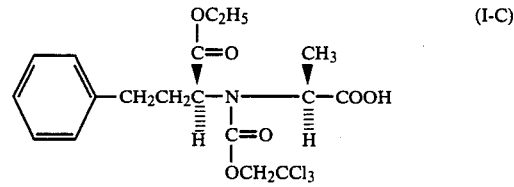

(I-C)

was prepared as follows:

To a mixture of N[(1S)-ethoxycarbonyl-3-phenylpropyl]-L-alanine (10 g) and sulfuric acid (10 ml) in 100 ml of dioxane was added 150 ml of isobutylene, and the resulting reaction mixture was shaken in a pressure bottle overnight. The reaction mixture was neutralized with 50% NaOH, taken up in 200 ml of ethyl acetate, and washed with water. The organic solution was dried and evaporated to dryness to give 10 g of oily product (I-A), N-[(1S)-Ethoxycarbonyl-3-phenylpropyl]-L-alanine t-butyl ester.

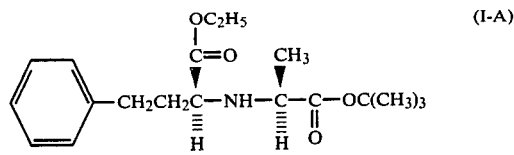

A mixture containing 2.52 g (7.51 mmol) of compound (I-A), 1.10 ml (7.99 mmol) of 2,2,2-trichloroethyl chloroformate, and 1.0 ml (12.4 mmol) of pyridine in 25 ml of dry tetrahydrofuran was refluxed under a nitrogen atmosphere for 3 hours. The reaction mixture was filtered, taken up in 200 ml of ether, and washed four times with 1N hydrochloric acid and once with brine. The organic phase was dried over MgSO$_4$, filtered, and concentrated in vacuo to yield 3.79 g (99%) of compound (I-B), N-[(1S)-1-ethoxycarbonyl-3-phenylpropyl]-N-(2,2,2-trichloroethoxycarbonyl)-L-alanine t-butyl ester:

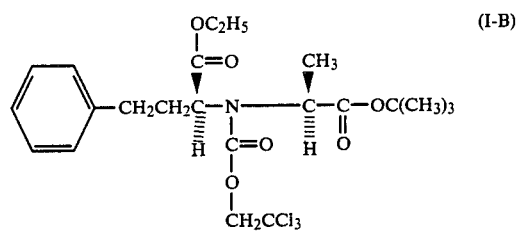

A mixture containing 1.98 g (3.88 mmol) of compound (I-B) in 25 ml of 4N HCl in dioxane at room temperature and under a nitrogen atmosphere was stirred for 8 hours. The mixture was then concentrated in vacuo to provide 1.77 g (100%) of compound (I-C).

EXAMPLE II

A 250 ml pyrex heavy-walled pressure bottle is charged with 50 ml of dioxane, 3 ml of concentrated sulfuric acid, 1.3 g (0.01 mole) of piperazic acid (II-A) and approximately 75 ml of isobutylene, liquified by passage into a large test-tube cooled in a dry ice-acetone bath. The bottle is closed with a rubber stopper, clamped securely in place, and is shaken mechanically at room temperature overnight. The bottle is chilled in an ice bath and opened. The contents are poured into a separatory funnel containing a cold mixture of 200 ml of ether and 125 ml of 1N sodium hydroxide. The aqueous layer is washed with ether. The combined ethereal solution is dried over sodium sulfate and evaporated under vacuum to afford an oil, which is dissolved in 25 ml of ether. Addition of dry hydrogen chloride gives 1.3 g of crystalline piperazic acid t-butyl ester dihydrochloride salt (II-B).

A mixture of 2.6 g (0.01 mole) of piperazic acid t-butyl ester dihydrochloride, ethyl iodine (1.6 g; 0.01 mole) and triethylamine (5 g, 0.05 mole) in 25 ml of THF is heated to reflux for 5 hours. After cooling, the reaction mixture is suction-filtered to remove the solids that form. The filtrate is concentrated under reduced pressure and diluted with ether. The ether solution is washed with water and dried over sodium sulfate. Removal of solvent affords an oily residue; this substance is purified by HPLC, using 4% ethyl acetate in hexane as the solvent system to give 0.7 g of 1-Ethyl-hexahydropyridazine-3-carboxylic acid t-butyl ester (II-C).

The reaction sequence is:

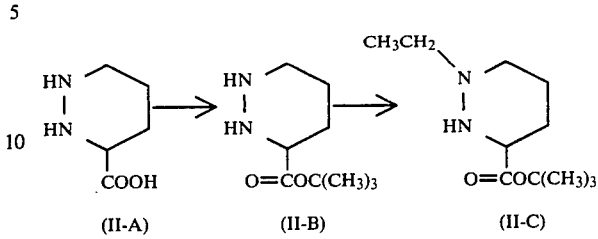

To a mixture containing 1.82 g (4 mmole) of compound (I-C) and 0.8 ml (9.2 mmol) of oxalyl chloride in 20 ml of methylene chloride at room temperature and under an inert atmosphere is added 20 μL (0.26 mmol) of N,N-dimethylformamide. After 2 hours the mixture is concentrated in vacuo and the residue dissolved in 10 ml of dry methylene chloride. To this mixture is added dropwise a solution containing 958 mg (4.48 mmol) of compound (II-C) and 1.2 ml (14.8 mmol) of pyridine in 10 ml of dry methylene chloride. After 16 hours the reaction mixture is diluted with 300 ml of ether and washed several times with water. The organic layer is dried (Na$_2$SO$_4$), concentrated in vacuo and purified by HPLC (10% ethylacetate in hexane) to give 1.4 g of compound (II-D), 2-N-[N-[(1S)-1-ethoxycarbonyl-3-phenylpropyl)]-N-(2,2,2-trichloroethoxycarbonyl)-L-alanyl]-1-N-ethylhexahydro-pyridazine-3-carboxylic acid, t-butyl ester.

To a mixture containing 1.4 g (2.15 mmol) of compound (II-D) in 15 ml of glacial acetic acid under nitrogen atmosphere is added 2.17 grams (33 mmol) of zinc dust. After 2.5 hours the mixture is filtered through celite and concentrated in vacuo. The residue is taken up in ether and washed with saturated aqueous sodium bicarbonate and water. The organic solution is dried (magnesium sulfate), filtered and concentrated in vacuo. Purification on HPLC (15% ethylacetate in hexane) gives 712 mg (1.5 mmol, 70%) of compound (II-E) as an oil, 2-N-[N-[(1S)-1-ethoxycarbonyl-3-phenylpropyl]-L-alanyl]-1-N-ethyl-hexahydropyridazine-3-carboxylic acid, t-butyl ester.

A solution of 712 mg (1.5 mmol) of compound (II-E) in 50 ml of ether is cooled in an ice water bath and anhydrous hydrogen chloride is bubbled through the solution slowly. After four hours, the solution is concentrated in vacuo at below 5° C. to give 580 mg (1.4 mmol) of compound (II-F), 2-N-[N-[(1S)-1-ethoxycarbonyl-3-phenylpropyl]-L-alanyl]-1-N-ethylhexahydropyridazine-3-carboxylic acid, as an HCl salt.

The reaction sequence is:

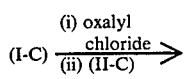

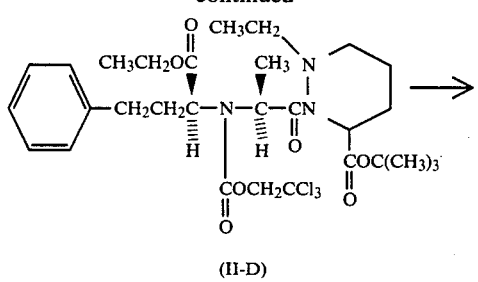

(II-D)

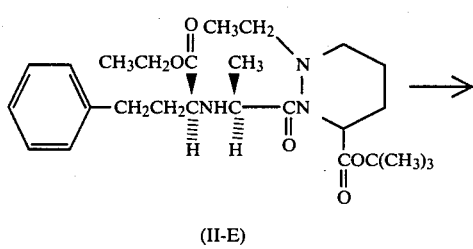

(II-E)

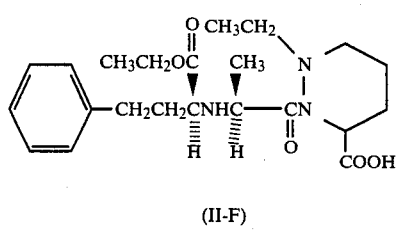

(II-F)

EXAMPLE III

Treatment of 2.6 g (0.01 mole) of the dihydrochloride compound (II-B) with an equal molar amount of benzyl bromide (1.7 g) under conditions similar to those used in forming compound (II-C) gives, after HPLC purification, 1.g of compound (III-A), 1-benzyl-hexahydropyridazine-3-carboxylic acid t-butyl ester:

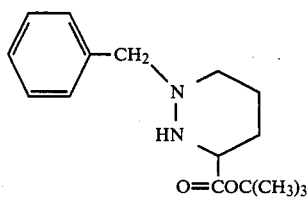

(III-A)

Compound (I-C) is converted to the acid chloride and then reacted with compound (III-A), to form the 1-benzyl analog of the 1-ethyl compound (II-D), by steps analogous to those employed to form compound (II-D). This 1-benzyl analog is converted to the de-N-protected t-butyl ester (III-B), and then to the acid (III-C), by steps wholly analogous to those used to produce compounds (II-E) and (II-F):

(III-B): 1-N-Benzyl-2-N-[N-[(1S)-1-ethoxycarbonyl-3-phenylpropyl]-L-alanyl]-hexahydropyridazine-3-carboxylic acid-t-butyl ester:

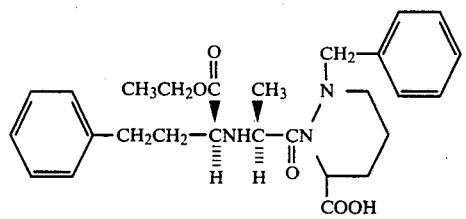

(III-C): 1-N-Benzyl-2-N-[N-[(1S)-1-ethoxycarbonyl-3-phenylpropyl]-L-alanyl]-hexahydropyridazine-3-carboxylic acid:

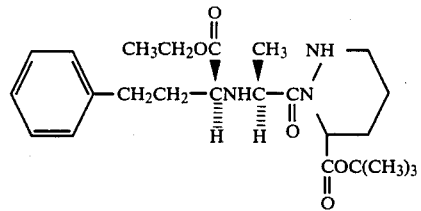

EXAMPLE IV

Employing procedures wholly analogous to those employed in Example III, compound (I-C) and compound (II-B) are reacted to form an N-protected, esterified intermediate which is de-N-protected to form compound (IV-A), which is then de-esterified to form compound (IV-B):

(IV-A): 2-N-[N-[(1S)-1-ethoxycarbonyl-3-phenylpropyl]-L-alanyl]-hexahydropyridazine-3-carboxylic acid-t-butyl ester:

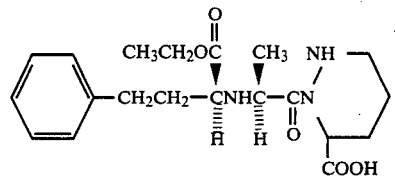

(IV-B): 2-N-[N-[(1S)-1-ethoxycarbonyl-3-phenylpropyl]-L-alanyl]-hexahydropyridazine-3-carboxylic acid:

EXAMPLE V

A mixture of 2-methyl-1,2,3,4-tetrahydrophthalazine-4-one (16.2 g; 0.1 mole) (compound V-A) and potassium cyanide (7.8 g; 0.12 mole) in 80 ml of DMF is heated at 70° C. for 6 hours. After cooling to room temperature, DMF is removed in vacuo. The resulting mixture is purified on a dry column to give 7.7 g of the compound (V-B), 4-cyano-2-methyl-1,2-dihydrophthalazine, as an oil.

A mixture of 10 g (0.058 mole) of compound (V-B) and 25 g of hydrochloric acid is refluxed for about three hours and the solution was evaporated to dryness in vacuo. The residue is stirred thoroughly with 200 ml of 95% ethanol. After filtration the filtrate is evaporated to give 9.2 g of crude 2-methyl-1,2-dihydrophthalazine-4-carboxylic acid hydrochloride salt (compound V-C). Treatment of this substance with isobutylene by a procedure similar to that described in Example II for the preparation of compound (II-B) gives, after purification, (by HPLC, 2% ethyl acetate in hexane), 1.9 g of compound (V-D), 2-methyl-1,2-dihydrophthalazine-4-carboxylic acid, t-butyl ester.

A mixture of 1.9 g (7.7 mole) of compound (V-D) and 1 gram of 5% palladium on charcoal in 50 ml of ethanol is shaken on a Parr hydrogenation apparatus for 3 hours. After filtration, the filtrate is concentrated and chromatographed on a dry column (hexane:ethylacetate, 1:1) to give 0.8 g of the compound (V-E), 2-methyl-1,2,3,4-tetrahydro-phthalazine-4-carboxylic acid, t-butyl ester, as an oil. The reaction sequence is:

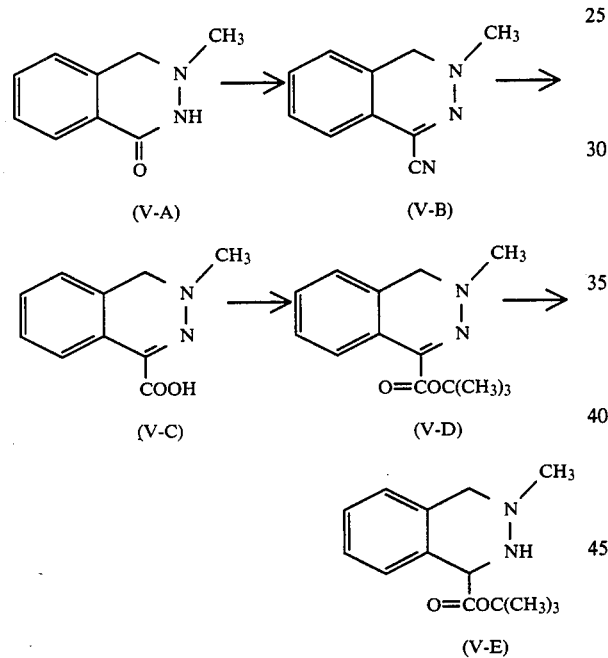

Employing procedures wholly analogous to those employed in Example III, compound (I-C) and compound (V-E) are reacted to form an N-protected, esterified compound which is de-N-protected to form compound (V-F) which is de-esterified to form compound (V-G).

(V-F): 3-N-[N-[(1S)-1-ethoxycarbonyl-3-phenylpropyl]-L-alanyl]-2-N-methyl-1,2,3,4-tetrahydrophthalazine-4-carboxylic acid, t-butyl ester:

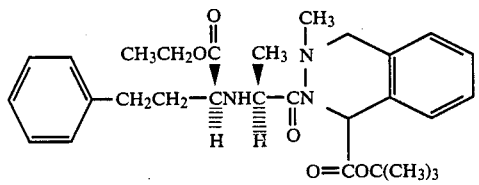

(V-G): 3-N-[N-[(1S)-1-ethoxycarbonyl-3-phenylpropyl]-L-alanyl]-2-N-methyl-1,2,3,4-tetrahydrophthalazine-4-carboxylic acid:

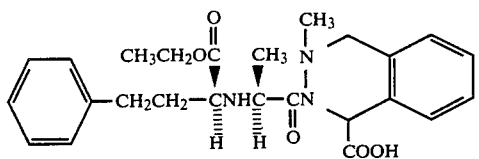

EXAMPLES VI-XII

The following compounds and their t-butyl esters are prepared by methods wholly analogous to the methods described in Example III.

(VI): 2-N-[N-[(1S)-1-ethoxycarbonyl-3-phenylpropyl]-L-alanyl]-1-N-phenylhexahydropyridazine-3-carboxylic acid

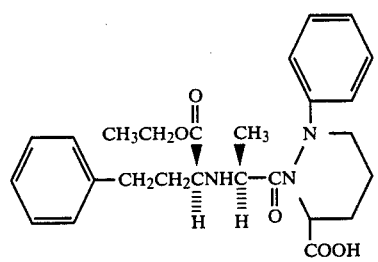

(VII): 2-N-[N-[(1S)ethoxycarbonylethyl]-L-alanyl]-1-N-methyl-hexahydropyridazine-3-carboxylic acid

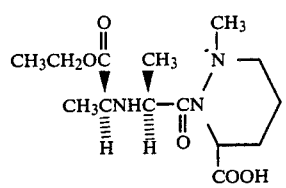

(VIII): 2-N-[N-[(1S)-1-ethoxycarbonyl-3-phenylpropyl]-L-lysinyl]-1-N-methyl-hexahydropyridazine-3-carboxylic acid

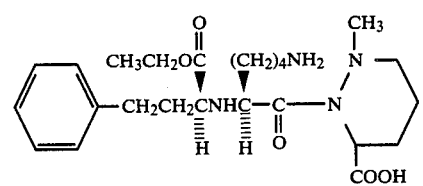

(IX): 2-N-[N-[(1S)-1-ethoxycarbonyl-3-phenylpropyl]-L-alanyl]-6-one-1-N-phenyl-hexahydropyridazine-3-carboxylic acid

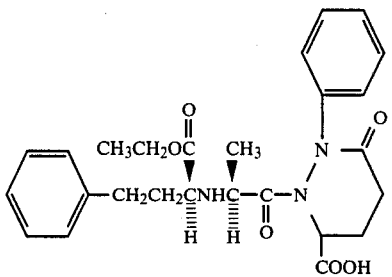

(X): 1-N-[N-[(1S)-1-ethoxycarbonyl-3-phenylpropyl]-L-alanyl]-4,5-dihydropyrazole-5-carboxylic acid

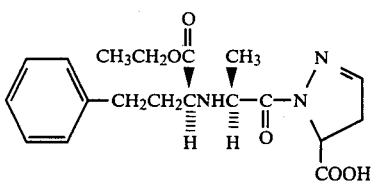

(XI): 2-N-[N-[(1S)-1-ethoxycarbonyl-3-phenylpropyl]-L-alanyl]-1-N-methyl-6-one-hexahydropyridazine-3-carboxylic acid

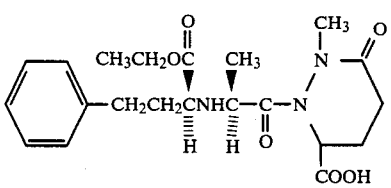

(XII:) 2-N-[N-[(1S)-1-ethoxycarbonyl-3-phenylpropyl]-L-alanyl]-1-N-(4-pyridyl)-hexahydropyridazine-3-carboxylic acid

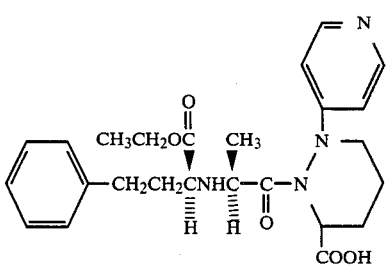

What is claimed is:

1. Compounds of the formula

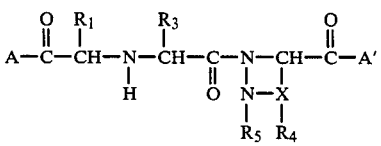

and pharmaceutically acceptable salts thereof, wherein
X is a chain of 3 carbon atoms;
A and A' are independently hydroxy or $C_{1-9}$ alkoxy;
$R_1$ is hydrogen, $C_{1-9}$ alkyl, phenyl or phen $C_{1-9}$ alkyl;
$R_3$ is hydrogen, $C_{1-9}$ alkyl, or w-amino $C_{1-9}$ alkyl;
$R_4$ is hydrogen, phenyl, phen $C_{1-9}$ alkyl, $C_{3-9}$ cycloalkyl, or phenyl fused to the ring containing X to form a phthalazine; and
$R_5$ is hydrogen, $C_{1-9}$ alkyl, phenyl or phen $C_{1-9}$ alkyl.

2. The compound according to claim 1 which is 2-N-[N-[(1S)-1-ethoxycarbonyl-3-phenylpropyl]-L-alanyl]-1-N-ethylhexahydropyridazine-3-carboxylic acid, and its pharmaceutically acceptable salts.

3. The compound according to claim 1 which is 2-N-[N-[(1S)-1-ethoxycarbonyl-3-phenylpropyl]-L-alanyl]-1-N-ethylhexahydropyridazine-3-carboxylic acid t-butyl ester, and its pharmaceutically acceptable salts.

4. The compound according to claim 1 which is 1-N-Benzyl-2-N-[N-[(1S)-1-ethoxycarbonyl-3-phenylpropyl]-L-alanyl]hexahydropyridazine-3-carboxylic acid, and its pharmaceutically acceptable salts.

5. The compound according to claim 1 which is 1-N-Benzyl-2-N-[N-[(1S)-1-ethoxycarbonyl-3-phenylpropyl]-L-alanyl]hexahydropyridazine-3-carboxylic acid t-butyl ester, and its pharmaceutically acceptable salts.

6. The compound according to claim 1 which is 2-N-[N-[(1S)-1-ethoxycarbonyl-3-phenylpropyl]-L-alanyl]-hexahydropyridazine-3-carboxylic acid, and its pharmaceutically acceptable salts.

7. The compound according to claim 1 which is 2-N-[N-[(1S)-1-ethoxycarbonyl-3-phenylpropyl]-L-alanyl]-hexahydropyridazine-3-carboxylic acid t-butyl ester, and its pharmaceutically acceptable salts.

8. The compound according to claim 1 which is 3-N-[N-[(1S)-1-ethoxycarbonyl-3-phenylpropyl]-L-alanyl]-2-N-methyl-1,2,3,4-tetrahydrophthalazine-4-carboxylic acid, and its pharmaceutically acceptable salts.

9. The compound according to claim 1 which is 3-N-[N-[(1S)-1-ethoxycarbonyl-3-phenylpropyl]-L-alanyl]-2-N-methyl-1,2,3,4-tetrahydrophthalazine-4-carboxylic acid t butyl-ester, and its pharmaceutically acceptable salts.

10. Compounds according to claim 1 selected from the group consisting of 2-N-[N-[(1S)-1-ethoxycarbonyl-3-phenylpropyl]-L-alanyl]-1-N-phenyl-hexahydropyridazine-3-carboxylic acid, its lower alkyl esters, and pharmaceutically acceptable salts thereof.

11. Compounds according to claim 1 selected from the group consisting of 2-N-[N-[(1S)ethoxycarbonylethyl]-L-alanyl]-1-N-methyl-hexahydro-pyridazine-3-carboxylic acid, its lower alkyl esters, and pharmaceutically acceptable salts thereof.

12. Compounds according to claim 1 selected from the group consisting of 2-N-[N-[(1S)-1-ethoxycarbonyl-3-phenylpropyl]-L-lysinyl]-1-N-methyl-hexahydropyridazine-3-carboxylic acid, its lower alkyl esters, and pharmaceutically acceptable salts thereof.

13. Compounds according to claim 1 selected from the group consisting of 2-N-[N-[(1S)-1-ethoxycarbonyl-3-phenylpropyl]-L-alanyl]-6-one-1-N-phenyl-hexahydropyridazine-3-carboxylic acid, its lower alkyl esters, and pharmaceutically acceptable salts thereof.

14. Compounds according to claim 1 selected from the group consisting of 2-N-[N-[(1S)-1-ethoxycarbonyl-3-phenylpropyl]-L-alanyl]-1-N-methyl-6-one-hexahydropyridazine-3-carboxylic acid, its lower alkyl esters, and pharmaceutically acceptable salts thereof.

15. Compounds according to claim 1 selected from the group consisting of 2-N-[N-[(1S)-1-ethoxycarbonyl-3-phenylpropyl]-L-alanyl]-1-N-(4-pyridyl)-hexahydropyridazine-3-carboxylic acid, its lower alkyl esters, and pharmaceutically acceptable salts thereof.

16. The compounds according to claim 1 having an (S,S) structural configuration.

17. An antihypertensive pharmaceutical preparation comprising one or more compounds or salts according to claim 1 in association with a pharmaceutically acceptable carrier.

18. The method of alleviating hypertension in a host suffering therefrom, comprising administering to said host a therapeutically effective amount of one or more compounds or salts according to claim 1.

* * * * *